(12) United States Patent
Wang et al.

(10) Patent No.: US 12,070,246 B1
(45) Date of Patent: Aug. 27, 2024

(54) AUXILIARY IMPLANTATION ASSEMBLY, KIT, AND SYSTEM FOR FLEXIBLE NEURAL ELECTRODES

(71) Applicant: Beijing BCIFlex Medical Technology Co., Ltd., Beijing (CN)

(72) Inventors: Dawei Wang, Beijing (CN); Jinfen Wang, Beijing (CN); Huihui Tian, Beijing (CN); Guiqiang Yang, Beijing (CN); Qian Li, Beijing (CN)

(73) Assignee: BEIJING BCIFLEX MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/626,468

(22) Filed: Apr. 4, 2024

(30) Foreign Application Priority Data

Jun. 16, 2023 (CN) .......................... 202310712671.X

(51) Int. Cl.
*A61B 17/34* (2006.01)
*A61N 1/05* (2006.01)

(52) U.S. Cl.
CPC ........ *A61B 17/3468* (2013.01); *A61N 1/0534* (2013.01)

(58) Field of Classification Search
CPC .......................... A61B 17/3468; A61N 1/0534
See application file for complete search history.

(56) References Cited

U.S. PATENT DOCUMENTS

| 11,878,176 B2 * | 1/2024 | Boggs ................ A61B 17/3468 |
| 2007/0255371 A1 | 11/2007 | Bonde |
| 2018/0296243 A1 | 10/2018 | Hanson |
| 2022/0016432 A1 * | 1/2022 | Boggs ................ A61N 1/36125 |

(Continued)

FOREIGN PATENT DOCUMENTS

| CN | 1283128 A | 2/2001 |
| CN | 108903916 A | 11/2018 |
| CN | 114788700 A | 7/2022 |

(Continued)

OTHER PUBLICATIONS

Chinese Decision to Grant a Patent issued in corresponding CN Patent Application No. 202310712671.X, dated Aug. 8, 2023, with English translation.

(Continued)

*Primary Examiner* — Phong Son H Dang
(74) *Attorney, Agent, or Firm* — Carter, DeLuca & Farrell LLP

(57) ABSTRACT

The present application provides an auxiliary implantation assembly, kit and system for flexible neural electrode, comprising: a cannula having a longitudinal cavity, and a tube wall at the distal end of the cannula configured to form a contact area larger than a first threshold to realize the pressing and limiting against the distal part in a case where the cannula is fixed and contacts the distal part of the flexible neural electrode; and a traction member extending in the longitudinal direction, the distal end of which is formed with a traction part and is configured to form a first physical connection mechanism with the proximal end of the cannula, the first physical connection mechanism is switchable between a locked state and an unlocked state by means of the proximal operation of the traction member.

20 Claims, 8 Drawing Sheets

(56) References Cited

U.S. PATENT DOCUMENTS

2022/0133353 A1* 5/2022 Kim ................ A61B 17/3468
623/15.11

FOREIGN PATENT DOCUMENTS

| CN | 115054335 A | 9/2022 |
| CN | 115671541 A | 2/2023 |
| CN | 218500724 U | 2/2023 |

OTHER PUBLICATIONS

Chinese Office Action issued in corresponding CN Patent Application No. 202310712671.X, dated Jul. 22, 2023, with English translation.

* cited by examiner

AUXILIARY IMPLANTATION ASSEMBLY, KIT, AND SYSTEM FOR FLEXIBLE NEURAL ELECTRODES

CROSS REFERENCE TO RELATED APPLICATIONS

The present application claims the benefit of and priority to Chinese Patent Application No. 202310712671.X, filed Jun. 16, 2023, the entire contents of which is hereby incorporated by reference.

TECHNICAL FIELD

The present application relates to the implantation of flexible neural electrodes, specifically concerning an auxiliary implantation assembly, kit, and system designed for such electrodes.

BACKGROUND

Flexible neural electrodes are research subjects of great concern in the field of biomedical engineering. Their implantation offers essential technical support for fundamental research and clinical applications in fields including neurology, physiology, and neuroscience. Owing to the inherent low rigidity of flexible neural electrodes, they are prone to bending and deformation during implantation, necessitating the use of a rigid auxiliary implantation approach. In the process of rigid-assisted implantation of flexible neural electrodes, the precise relative positioning of the electrodes in relation to the implant sites is crucial, because it directly influences the electrodes' efficacy in recording or stimulating neural activity within the nervous system. For instance, during deep brain stimulation treatments for Parkinson's disease, these electrodes are employed to convey electrical charges to specific neural nuclei. If the electrodes are not accurately implanted into the targeted brain regions, it could lead to a diminished effect of electrical stimulation, thereby compromising the treatment's efficacy. Furthermore, in brain-computer interface research, flexible neural electrodes are instrumental in recording neural signals from specific brain regions and transmitting these signals for computational analysis. Imprecise electrode placement can lead to inaccurate measurement of neural activity in these regions, adversely affecting the precision in identifying and interpreting neural signals. Hence, precise electrode implantation is imperative for both accurate signal recording and modulation.

Contemporary research is committed to the development of more sophisticated neural electrodes, aimed at enhancing their capacity to efficiently capture neural signals and generate a more pronounced stimulatory impact on neural nuclei. In pursuit of this objective, many studies are being conducted, including the optimization of electrode materials, shapes, and dimensions, along with the characterization of electrical properties and the optimization of assembly methods. However, the current commercial offerings of flexible neural electrodes exhibit certain limitations in terms of implantation precision and operability.

At present, various methods exist for the implantation of flexible neural electrodes. A notable technique involves pre-implantation curing of the electrodes to induce rigidity, followed by a return to their flexible state during the actual implantation process. However, this method has its drawbacks. Controlling the duration of the curing-to-softening transition is a complex task; moreover, the shift from a rigid to a flexible state can alter the configuration of the electrodes' implantable segment, consequently affecting their relative positioning to the target implant sites.

SUMMARY OF THE INVENTION

The present application addresses and solves the above-mentioned problems in existing technologies. The purpose of the present application is to provide an auxiliary implantation assembly, kit, and system for flexible neural electrodes. This innovation is designed to enable the effective insertion of flexible neural electrodes into targeted areas, achieving both precision and ease of operation in the implantation process. Additionally, it ensures that the morphology of the electrode's implanted segment and its positioning relative to the target site remain unaffected throughout and after the implantation procedure.

According to a first aspect of the present application, an auxiliary implantation assembly for a flexible neural electrode is provided. The auxiliary implantation assembly comprises a cannula and a traction member extending in the longitudinal direction. The cannula has a longitudinal cavity, and the tube wall at the distal end of the cannula is configured to form a contact area larger than a first threshold to realize the pressing and limiting against the distal part, in a case where the cannula is fixed and contacts with the distal part of the flexible neural electrode. The traction member is formed with a traction part at the distal end and is configured to form a first physical connection mechanism with the proximal end of the cannula, the first physical connection mechanism is switchable between a locked state and an unlocked state by means of the proximal operation of the traction member. Wherein, in the locked state, the traction part penetrates out of the distal end of the cannula, and the penetrated traction part is configured to form a second physical connection mechanism with the distal part of the flexible neural electrode so as to guide the flexible neural electrode in implantation. In the unlocked state, the traction member is movable in the longitudinal direction along the cavity of the cannula, the second physical connection mechanism is configured to separate in a case where a proximal force is applied to the traction member.

According to a second aspect of the present application, a flexible neural electrode implantation kit is provided. The flexible neural electrode implantation kit comprises a flexible neural electrode and the auxiliary implantation assembly according to various embodiments of the present application. The flexible neural electrode contains a layout part of an electrode site and a connection part distal to the layout part. The auxiliary implantation assembly comprises a cannula and a traction member extending in the longitudinal direction. The cannula has a longitudinal cavity, and the tube wall at the distal end of the cannula is configured to form a contact area larger than a first threshold to realize the pressing and limiting against the distal part in a case where the cannula is fixed and contacts the distal part of the flexible neural electrode. The traction member is formed with a traction part at the distal end and is configured to form a first physical connection mechanism with the proximal end of the cannula, the first physical connection mechanism is switchable between a locked state and an unlocked state by means of the proximal operation of the traction member. Wherein, in the locked state, the traction part penetrates out of the distal end of the cannula, and the penetrated traction part is configured to form a second physical connection mechanism with the distal part of the flexible neural electrode so as to guide the flexible neural electrode in implantation. In the unlocked state, the traction member is movable in the longitudinal direction along the cavity of the cannula, the second physical connection mechanism is configured to separate in a case where a proximal force is applied to the traction member.

According to a third aspect of the present application, a flexible neural electrode implantation system is provided. The system comprises the flexible neural electrode implantation kit according to various embodiments of the present application and a secondary fixing device. The flexible neural electrode comprises a proximal end part connected with the layout part via an interconnection lead. The secondary fixing device comprises a base, and a first fixing part and a second fixing part which are respectively detachably locked to the base, wherein the first fixing part is configured to fix the proximal part of the cannula, and the second fixing part is configured to fix the proximal end part of the flexible neural electrode. The flexible neural electrode implantation kit comprises a flexible neural electrode and the auxiliary implantation assembly according to various embodiments of the present application. The flexible neural electrode contains a layout part of an electrode site and a connection part distal to the layout part. The auxiliary implantation assembly comprises a cannula and a traction member extending in the longitudinal direction. The cannula has a longitudinal cavity, and the tube wall at the distal end of the cannula is configured to form a contact area larger than a first threshold to realize the pressing and limiting against the distal part in a case where the cannula is fixed and contacts the distal part of the flexible neural electrode. The traction member is formed with a traction part at the distal end and is configured to form a first physical connection mechanism with the proximal end of the cannula, the first physical connection mechanism is switchable between a locked state and an unlocked state by means of the proximal operation of the traction member. Wherein, in the locked state, the traction part penetrates out of the distal end of the cannula, and the penetrated traction part is configured to form a second physical connection mechanism with the distal part of the flexible neural electrode, so as to guide the flexible neural electrode in implantation. In the unlocked state, the traction member is movable in the longitudinal direction along the cavity of the cannula, the second physical connection mechanism is configured to separate in a case where a proximal force is applied to the traction member.

In the present application, the locking-unlocking switchable design of the cannula and the traction member enables in the locked state, the cannula to connect and fix the traction member, and the flexible neural electrode can form a second physical connection structure with the traction part at the distal end of the traction member, so that the traction part can provide more stable and reliable guidance for the distal part of the flexible neural electrode, thus achieve an efficient, stable, safe and accurate implantation into the target site. Further, the cannula and the traction member can be unlocked after implantation. In the unlocked state, the second physical connection structure is conveniently separated, so that the traction member can be removed without affecting the position of the cannula, while the cannula can firmly press against the distal part of the flexible neural electrode to limit the position without displacement. Further, after the traction member is removed, the cannula and the flexible neural electrode are also separable from each other, so that removing the cannula then will not bring any displacement to the flexible neural electrode, it can be ensured that throughout the whole implantation process, either before or after the implantation process, the flexible neural electrode will neither be deformed in morphology nor displaced. In this way, it can accurately act on the target implantation area to obtain the expected measurement data or the best treatment effect. For example, in Parkinson's deep brain stimulation therapy, the flexible neural electrode is used to transfer charges to the neural nuclei in a specific area. In a case where the electrode does not move after implantation, it can ensure that the electrical stimulation acts on the target implantation area, thus significantly improving the curative effect. In addition, in the research of brain-computer interface, the flexible neural electrode is used to capture neural signals and transmit them to the computer for analysis. In a case where the electrode does not move after implantation, the signal quality can be ensured to be stable, thus improving the recognition and interpretation accuracy of neural signals.

BRIEF DESCRIPTION OF THE DRAWINGS

In the drawings, which are not necessarily drawn to scale, the same reference numerals may describe similar parts in different views. The same reference numerals with letter suffixes or different letter suffixes may indicate different examples of similar parts. The drawings generally illustrate various embodiments by way of example and not limitation, and together with the description and claims, serve to explain the disclosed embodiments. Appropriately, the same reference numerals are used throughout the drawings to refer to the same or similar parts. Such embodiments are illustrative and are not intended to be exhaustive or exclusive embodiments of the present device or method.

REFERENCE SIGN

Figure 1:
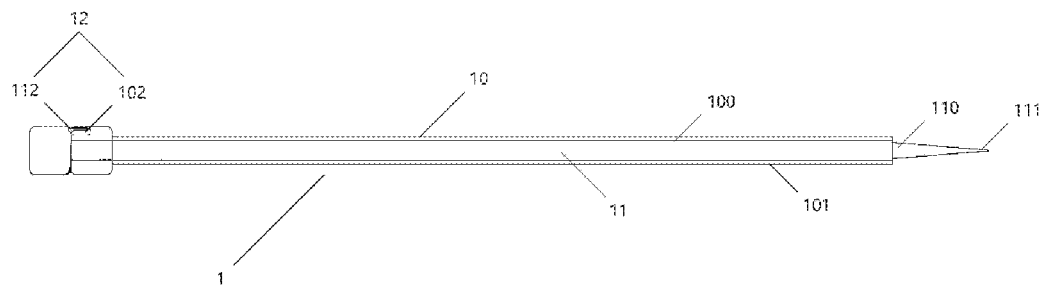
FIG. 1 is a structural schematic diagram of an auxiliary implantation assembly for a flexible neural electrode in a locked state according to an embodiment of the present application.

1—auxiliary implantation assembly,

10—cannula, 100—cavity, 101—tube wall, 102—snapping groove,
11—traction member, 110—traction part, 111—sharp head, 112—buckle,
12—snapping part,
2—flexible neural electrode,
20—connection part, 200—connection hole, 21—layout part, 210—electrode site,
22—interconnection lead, 23—proximal end part,
3—flexible neural electrode implantation kit,
4—flexible neural electrode implantation system,
40—secondary fixing device, 400—base, 401—first fixing part, 402—second fixing part, 403—longitudinal chute, 410—carriage, 411—connection hole,
5—target site.

DETAILED EMBODIMENTS

In order to enable those skilled in the art to better understand the technical solution of the present application, the present application will be described in detail with the drawings and specific embodiments. The embodiments of the present application will be described in further detail below with reference to the drawings and specific embodiments, but not as a limitation of the present application.

The terms such as "first", "second" used in the present application do not indicate any order, quantity or importance, but are only used to distinguish different parts. The expressions "first" and "second" are only numbered for convenience, and are not intended to imply that "first member" and "second member" must have different physical properties. Actually, the "first member" and "second member" may have the same or different structures, which are not limited to here, as long as the "first member" and "second member" are separate members. Further, the "first member" and "second member" may not even be separate members, but may be integrated into the same member, or may be substituted for each other, provided that the context is fully explained.

In the present application, when it is described that a specific device is located between a first device and a second device, there may or may not be an intervening device between the specific device and the first device or the second device. When it is described that a specific device is connected to other device, the specific device may be directly connected to the other device without an intervening device, or may not be directly connected to the other device but with an intervening device.

Similar words such as "comprising" or "containing" mean that the elements before the word cover the elements listed after the word, and the possibility of covering other elements is not excluded. "Up", "Down", "Left" and "Right" are only used to indicate the relative position relationship. When the absolute position of the described object changes, the relative position relationship may also changes accordingly.

In the present application, the term "proximal" is intended to mean a side close to an operator (such as a doctor) who performs an implantation operation, while the term "distal" is intended to mean a side close to a target site where a flexible neural electrode is to be implanted.

All terms (including technical terms or scientific terms) used in the present application have the same meanings as those understood by ordinary technicians in the field to which the present application belongs, unless otherwise defined. It should also be understood that terms defined in, for example, general dictionaries should be interpreted as having meanings consistent with their meanings in the context of the related art, and should not be interpreted in an idealized or extremely formal sense unless explicitly defined here. Techniques, methods and equipment known to those skilled in the related art may not be discussed in detail, but they should be regarded as part of the specification under appropriate circumstances.

Figure 2:
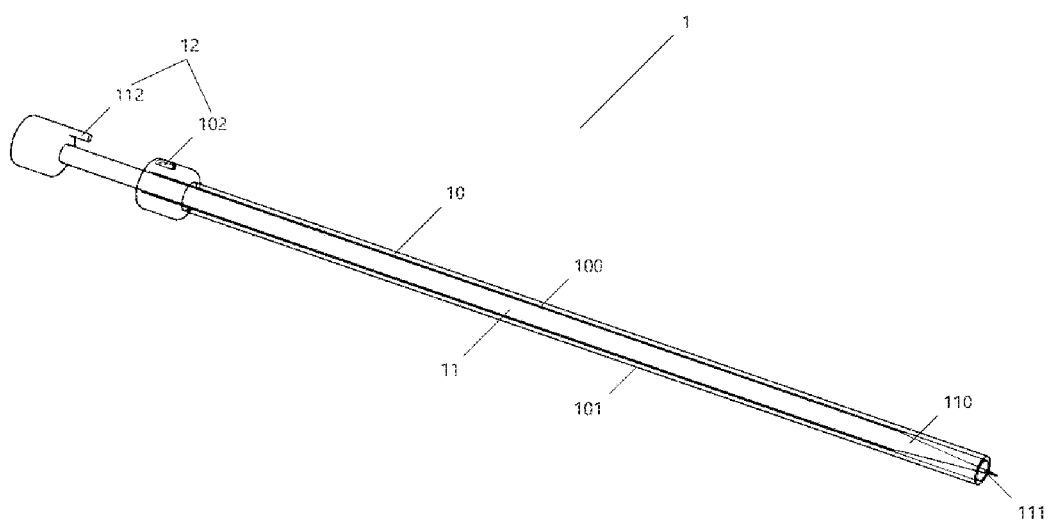
FIG. 2 is a structural schematic diagram of an auxiliary implantation assembly for a flexible neural electrode in an unlocked state according to an embodiment of the present application.

An embodiment of the present application provides an auxiliary implantation assembly 1 for a flexible neural electrode. As shown in FIGS. 1 and 2, the auxiliary implantation assembly 1 comprises a cannula 10 and a traction member 11. The flexible neural electrode here can be the flexible neural electrode 2 with the structure shown in FIG. 3, or the flexible neural electrode with other structures. In the embodiment of the present application, the flexible neural electrode 2 is described as an example of the flexible neural electrode. The cannula 10 has a longitudinal cavity 100, and the tube wall 101 at the distal end of the cannula 10 is configured to form a contact area larger than a first threshold value under the condition that the cannula 10 is fixed and contacts the distal part of the flexible neural electrode 2, so as to realize the pressing and limiting to the distal part. The first threshold can be set to be 15% or more, 20% or more, 30% or more of the surface area of the distal part of the flexible neural electrode 2, or it can be determined by pre-testing, as long as the contact area reaching this first threshold can realize the stable pressing and limiting of the cannula 10 to the distal part. The first threshold can vary with different structures and materials of the distal part, and can be determined according to the actual situation. The traction member 11 is a member extending in the longitudinal direction, and can be such as a traction guide wire, a traction needle. It has appropriate rigidity and flexibility so as to guide the flexible neural electrode 2 to perform implantation according to the required position and path. The distal end of the traction member 11 is formed with a traction part 110 and is configured to form a first physical connection mechanism with the proximal end of the cannula 10, and the first physical connection mechanism can be switched between a locked state as shown in FIG. 1 and an unlocked state as shown in FIG. 2 by means of the operation on the proximal side of the traction member 11. In some embodiments, the traction member 11 is made of precisely manufactured plastic and alloy materials, mainly including medical-grade plastic, metal and composite materials. Wherein, medical-grade plastics mainly have good biocompatibility, plasticity and formability, and are suitable for making small-diameter traction member 11. Because of its high strength and durability, metal materials are usually used to make large-diameter traction member 11. Composite materials combine the advantages of plastic and metal materials, and have good biocompatibility, high strength and rigidity, and can be used to make various types of traction members 11. Medical-grade plastic materials such as polyethylene, polypropylene, polystyrene and polyetherketone have good corrosion resistance, biocompatibility and manufacturability. Metal materials such as stainless steel, titanium alloy and aluminum alloy have excellent strength, rigidity and biocompatibility. Composite materials are composed of plastics and metals, including polyurethane, polycarbonate and polyamide, for example. These materials have good mechanical properties, biocompatibility and machinability, and have strong durability, corrosion resistance and high strength, which can withstand surgical treatment in vivo or will not be deformed or degraded when used. In addition, the traction part 110 adopts electrochemical etching as its processing method to meet the processing requirements with high precision.

In some embodiments, the first physical connection mechanism is a snapping part 12, which is composed of a buckle 112 located at the proximal end of the sharp head 111 and an snapping groove 102 located at the proximal end of the cannula 10. The buckle 112 is snapped with the snapping groove 102, so that the physical connection is realized. The snapping part 12 snaps, that is, when the buckle 112 snaps with the snapping groove 102, the traction part 11 is in a locked state, and the snapping part 12 does not snap, that is, when the buckle 112 is separated from the snapping groove 102, the traction part 11 is in an unlocked state. This is only an example, the first physical connection mechanism can also adopt different mechanical structures, such as but not limited to the detachable fitting of the slider-chute, the release/clamping of the pawl (grasper), the screwing of the internal and external threads, as long as it can be conveniently switched between the locked state and the unlocked state by means of the proximal operation of the traction member 11, such as but not limited to the operation of sliding, releasing the clamping, screwing.

As shown in FIG. 1, in the locked state, the traction part 110 penetrates out of the distal end of the cannula 10, and the penetrated traction part 110 is configured to form a second physical connection mechanism with the distal part of the flexible neural electrode 2, so as to guide the flexible neural electrode 2 to perform implantation. As shown in FIG. 2, in the unlocked state, the traction member 11 can move in the longitudinal direction along the cavity 100 of the cannula 10, and the second physical connection mechanism is configured to be separated in a case where a proximal force is applied to the traction member 11, that is, the traction member 11 is withdrawn from the cannula 10. That is to say, the force of withdrawing the traction member 11 itself can play a role in separating the second physical connection mechanism.

With the locking-unlocking switchable design of the cannula 10 and the traction member 11, in the locked state, the cannula 10 is connected and fixed with the traction member 11, and the flexible neural electrode 2 can form a second physical connection structure with the traction part 110 at the distal end of the traction member 11, so that the traction part 110 can provide more stable and reliable guidance for the distal part of the flexible neural electrode 2, so that it can be implanted into the target site efficiently, stably, safely and accurately. After implantation, the cannula 10 and the traction member 11 can be unlocked. In the unlocked state, the second physical connection structure is conveniently separated, so that the traction member 11 can be removed without affecting the position of the cannula 10, while the cannula 10 can be firmly pressed against the distal part of the flexible neural electrode 2 to limit the position without displacement. Further, after the traction member 11 is removed, the cannula 10 and the flexible neural electrode 2 are also separable from each other, so that removing the cannula 10 will not bring any displacement to the flexible neural electrode 2, so that it can be ensured that throughout the whole implantation process, either before or after the implantation process, the flexible neural electrode 2 will not be deformed in morphology or moved. In this way, its action site can accurately act on the target implantation area to obtain the expected measurement data or the best treatment effect. For example, in Parkinson's deep brain stimulation therapy, the flexible neural electrode 2 is used to transfer charges to the neural nuclei in a specific area. In a case where the electrode does not displace after implantation, it can ensure that the electrical stimulation acts on the target implantation area, thus significantly improving the treatment effect. In addition, in the research of brain-computer interface, the flexible neural electrode 2 is used to capture neural signals and transmit them to the computer for analysis. In a case where the electrode does not move after implantation, the signal quality can be ensured to be stable, thus improving the recognition and interpretation accuracy of neural signals.

Figure 3:
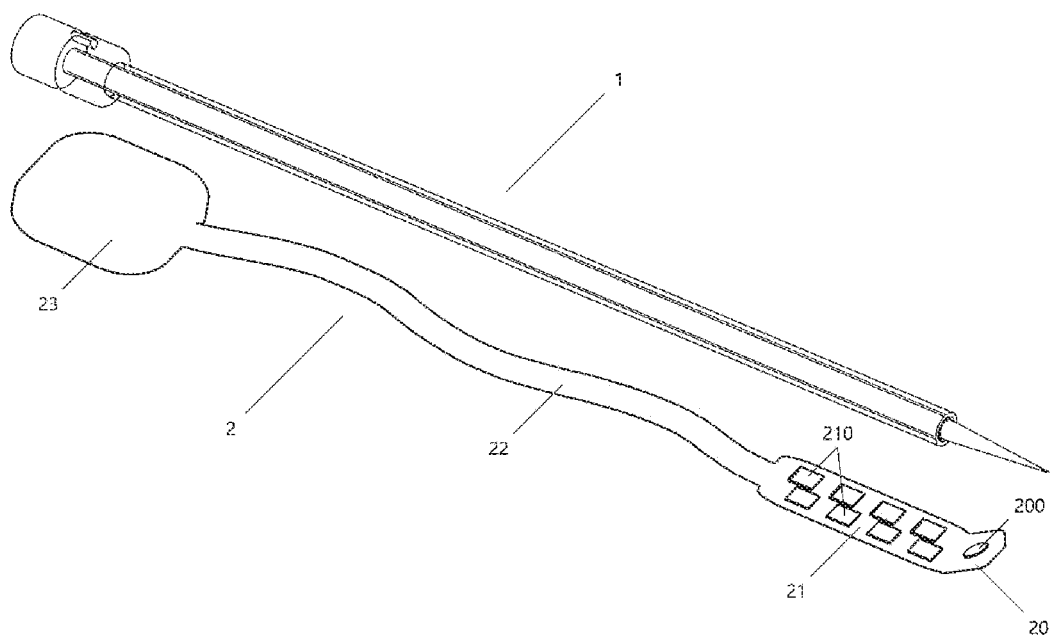
FIG. 3 is a structural diagram of a flexible neural electrode implantation kit according to an embodiment of the present application.

In some embodiments, the electrode site 210 are arranged or not arranged at the distal part of the flexible neural electrode 2 according to the layout mode of the electrode site 210, so that the separation of the second physical connection mechanism and the pressing and limiting of the cannula 10 will not interfere with the electrode site 210. For example, in a case where the layout of the electrode site 210 is submerged layout, the electrode site can be arranged at the distal part of the flexible electrode. On the other hand, as shown in FIG. 1, FIG. 2 and FIG. 3, the electrode site 210 may not be arranged at the distal part of the flexible neural electrode 2 (the curved part shown in FIG. 3), so that the traction of the flexible neural electrode 2 by the traction member 11 will not interfere with the electrode site 210.

In some embodiments, the auxiliary implantation assembly 1 is withdrawn in stages in a case where the layout part 21 of the electrode site 210 of the flexible neural electrode 2 is implanted into the target site 5. First, the snapping part 12 is switched to the unlocked state, and the traction member 11 is withdrawn proximally along the cavity 100 of the cannula 10 in the longitudinal direction. In the process of withdrawing the traction member 11 proximally relative to the target site 5, the cannula 10 contacts with the distal part of the flexible neural electrode 2 via the tube wall 101 at distal end to press and limit against the distal part. Then, after the traction member 11 is completely withdrawn from the target site 5, the cannula 10 is withdrawn from the target site 5 in the longitudinal direction. In this way, the morphology of the implanted part of the flexible neural electrode 2 and its position relative to the target site 5 will be not affected in the operation of withdrawing the auxiliary implantation assembly 1 after the flexible neural electrode 2 is implanted.

In some embodiments, the traction member 11 has a sharp head 111 to be inserted into the distal part of the flexible neural electrode 2, so as to form a second physical connection mechanism. The second physical connection mechanism realizes the detachable connection between the traction member 11 and the flexible neural electrode 2 in a simple physical connection way. By way of an example, the second physical connection mechanism can also adopt different physical connection structures, such as but not limited to adhesion between the traction part 110 and the distal part, the traction part 110 forms a grasper to grasp the distal part, as long as the detachable connection between the traction part 11 and the flexible neural electrode 2 can be realized in a simple physical connection manner. Note that the so-called "grasper" is intended to contain a structure of a base part and extension part(s) forming an inclined angle relative to the base part, which applies to the distal part, a force inclined relative to the surface of the distal part, so as to fix the distal part. Moreover, in order to ensure the connection reliability of the second physical connection mechanism, the sharp head 111 is configured to the length of the sharp head 111 in the longitudinal direction is greater than the thickness of the distal part of the flexible neural electrode 2. In the present embodiment, the length of the sharp head 111 in the longitudinal direction is 0.01-25 mm, and the cross-sectional diameter of the distal end is 0.01-25 mm, while the cross-sectional diameter of the proximal end should be consistent with the cross-sectional diameter of the middle segment of the traction member 11, for example, 0.01-25 mm.

In some embodiments, in a case where the flexible neural electrode 2 is to be implanted, the proximal end part 23 of the flexible neural electrode 2 is directly supported and fixed to the outer wall of the cannula 10, or supported and fixed to the same fixing device together with the cannula 10 in a detachable manner with respect to the cannula 10, in a way that the flexible neural electrode 2 is placed outside the cannula 10. By detachably connecting the flexible neural electrode 2 with the cannula 10 in a way that the flexible neural electrode 2 is placed outside the cannula 10, it can be realized that the relative position between the flexible neural electrode 2 and the target site 5 is not moved or the electrode is not damaged when the cannula 10 is withdrawn, and then the morphology of the implanted part of the flexible neural electrode 2 and its position relative to the target site 5 will not be affected when the auxiliary implantation assembly 1 is withdrawn after the flexible neural electrode 2 is implanted.

In some embodiments, the proximal end of the traction member 11 is configured to form a snapping part 12 with the proximal end of the cannula 10 to snap to the proximal end of the cannula 10. The snapping part 12 is any structure that can realize the snapping function, for example, it can be formed as a T-shaped part, so as to realize the detachable connection between the traction member 11 and the cannula 10 in a simple way, and the traction member 11 can be simply separated from the cannula 10 during withdrawal in stages. In addition, the length of the proximal limiting end of the T-shaped structure in the longitudinal direction is, for example, 1-25 mm, and the cross-sectional diameter of the proximal limiting end should be larger than that of the middle segment of the traction member 11 and the middle segment of the auxiliary implantation assembly 1, for example, the diameter is 1-25 mm.

Figure 4:
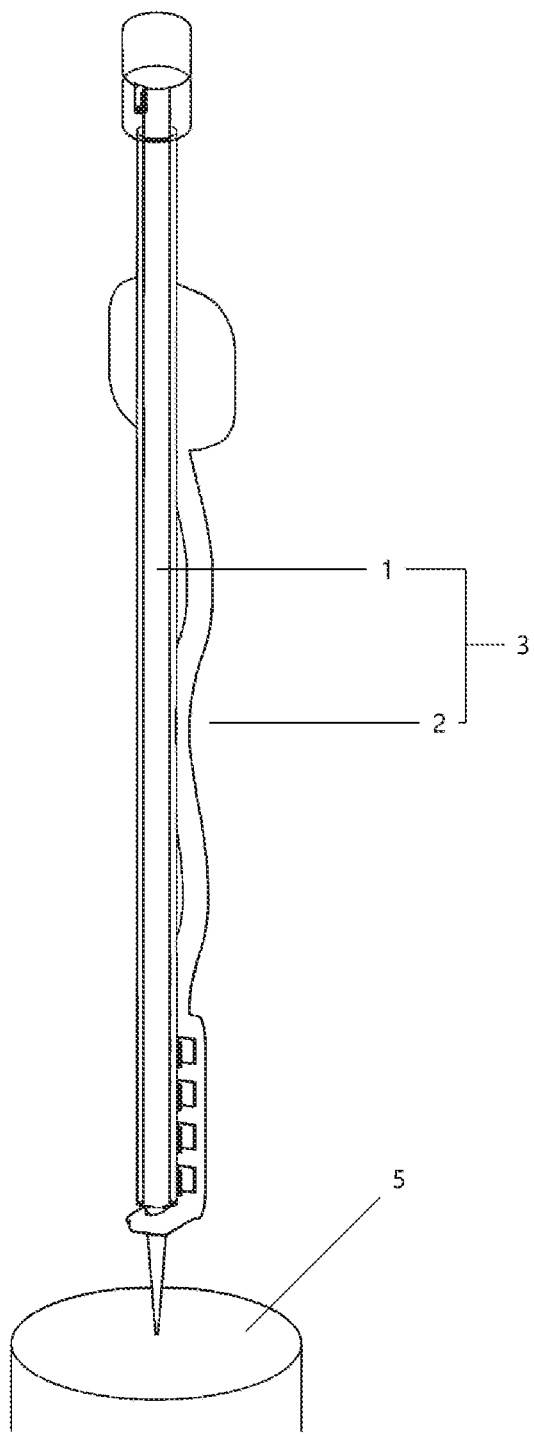
FIG. 4 is a structural schematic diagram of a flexible neural electrode implantation kit in a state before implanting the flexible neural electrode according to an embodiment of the present application.
Figure 5:
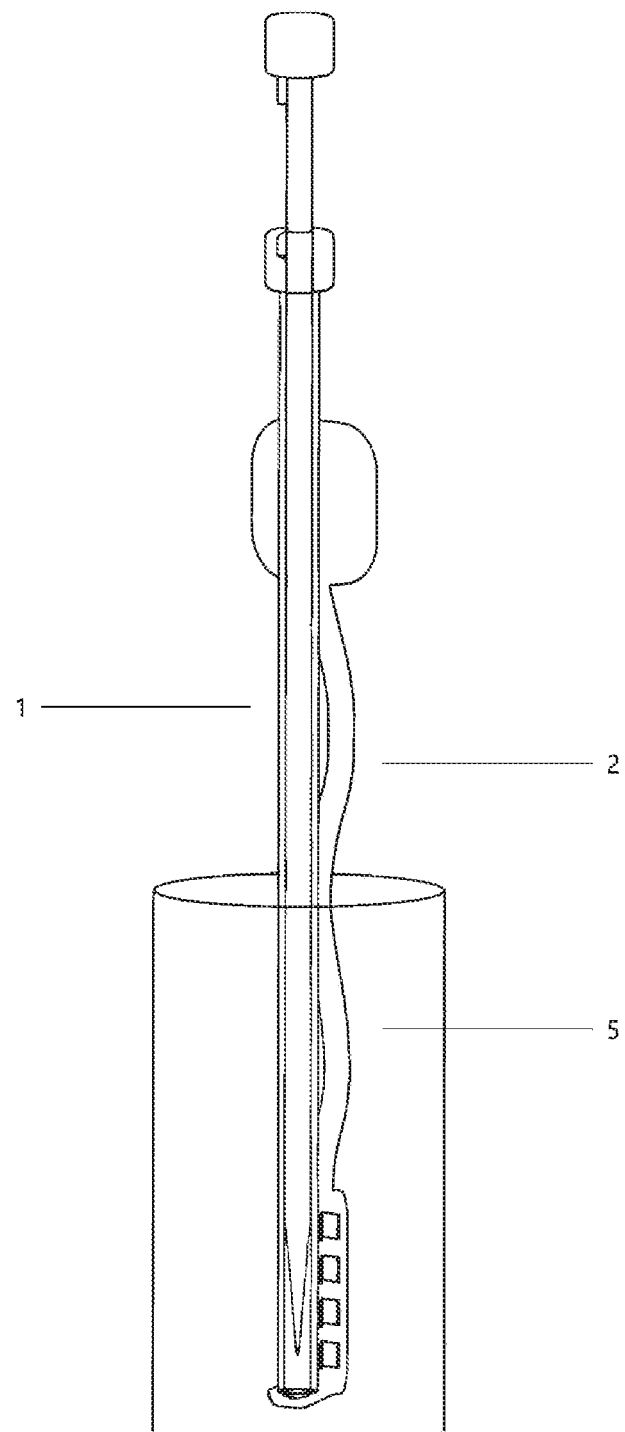
FIG. 5 is a structural schematic diagram of an auxiliary implantation assembly of the flexible neural electrode implantation kit in an unlocked state according to the embodiment of the present application.
Figure 6:
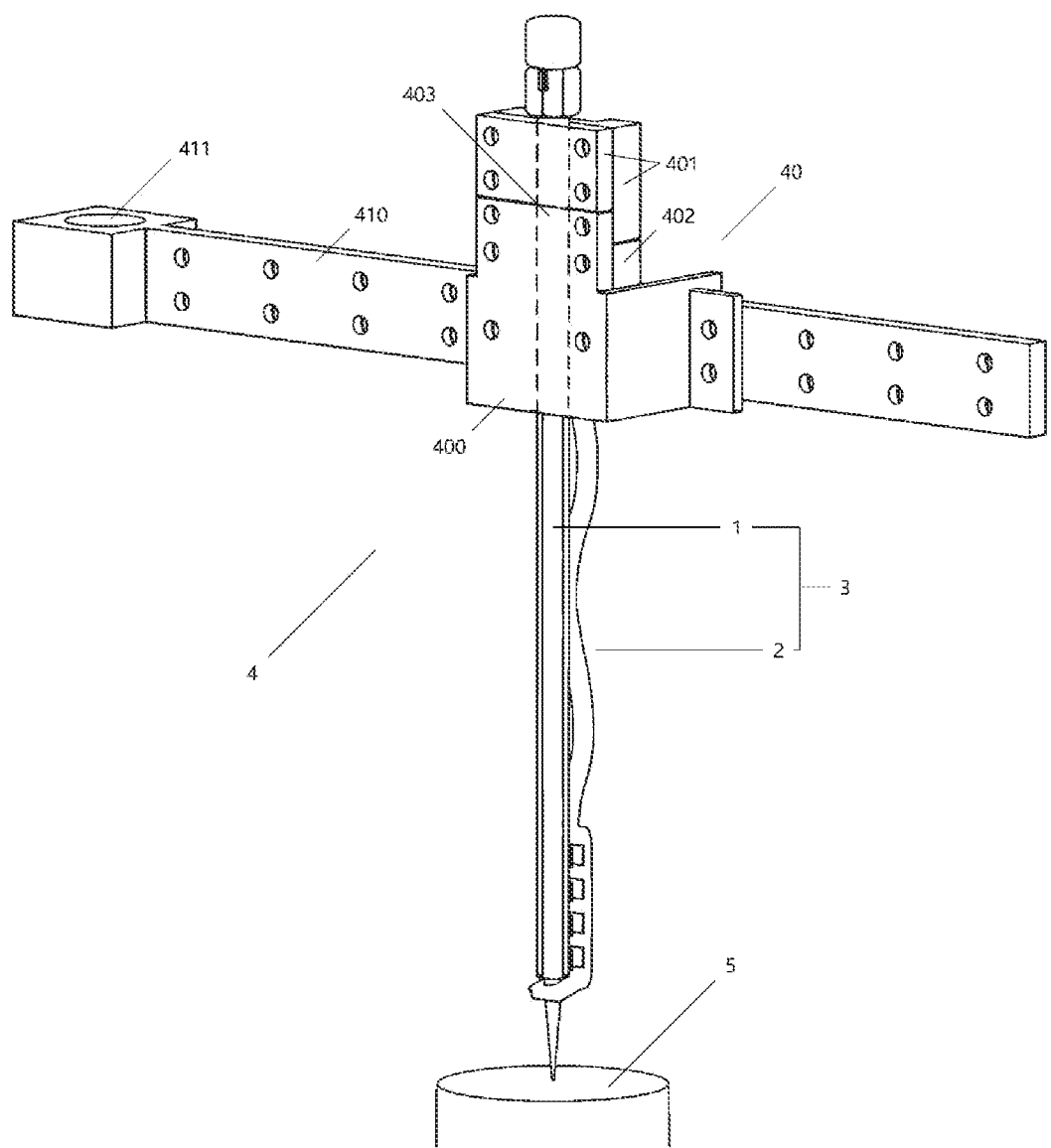
FIG. 6 is a structural schematic diagram of a flexible neural electrode implantation system in a state before implanting the flexible neural electrode according to an embodiment of the present application.

In some embodiments of the present application, a flexible neural electrode implantation kit 3 is provided. As shown in FIGS. 3 to 5, the flexible neural electrode implantation kit 3 of the present application comprises a flexible neural electrode 2 and an auxiliary implantation assembly 1 according to various embodiments of the present application. The flexible neural electrode 2 comprises a layout part 21 located at the distal end and containing a layout electrode site 210, and a connection part 20 distal to the layout part 21. The electrode site 210 may not be arranged on the connection part 20. The auxiliary implantation assembly 1 corresponds to the flexible neural electrode 2 one-by-one, and comprises a cannula 10 and a traction member 11. The cannula 10 has a longitudinal cavity 100, and the tube wall 101 at the distal end of the cannula 10 is configured to form a contact area larger than a first threshold in a case where the cannula 10 is fixed and contacts the distal part of the flexible neural electrode 2, so as to realize the pressing and limiting against the distal part. The traction member 11 is a member extending in the longitudinal direction, and can be such as a traction guide wire, a traction needle, and it has appropriate rigidity and flexibility so as to guide the flexible neural electrode 2 to perform implantation according to the required position and path. The distal end of the traction member 11 is formed with a traction part 110 and is configured to form a first physical connection mechanism with the proximal end of the cannula 10, and the first physical connection mechanism can be switched between a locked state as shown in FIG. 1 and an unlocked state as shown in FIG. 2 by means of the proximal operation of the traction member 11. Embodiments of the present application provide a composite structure of the flexible neural electrode 2 and the auxiliary implantation assembly 1, including one or more flexible neural electrodes 2 and auxiliary implantation assemblies 1, wherein a plurality of auxiliary implantation assemblies 1 are distributed in an array manner, so that the positions of the auxiliary implantation assemblies 1 can be arranged in advance according to the implantation requirements when implanting the flexible neural electrode 2, so as to improve the implantation position accuracy. For example, when implanting a plurality of flexible neural electrodes 2, 2-625 auxiliary implantation assemblies 1 are used and each auxiliary implantation assembly 1 is fixed in the longitudinal direction and arranged in an array manner. These assemblies are arranged an array with 1-25 rows and 1-25 columns in the horizontal direction. In some embodiments, the array of the auxiliary implantation assembly in the horizontal direction forms an angle with respect to the surface of the implanted object is 0-89.9°.

In some embodiments, each auxiliary implantation assembly 1 comprises a cannula 10 and a traction member 11 inserted into the cannula 10 in the longitudinal direction for assisting implantation. Each traction member 11 can move in the longitudinal direction in the cannula. Each traction member 11 comprises an auxiliary implantation end located at the distal end, that is, a traction part 110. The traction part 110 penetrates out of the distal end of the cannula 10 and is configured to be physically connected with the connection part 20 of the flexible neural electrode 2 to form a second physical connection mechanism.

In some embodiments of the present application, as shown in FIG. 4, in the flexible neural electrode implantation kit 3, the connection part 20 located at the distal implantation part of each flexible neural electrodes 2 can form a second physical connection mechanism with the auxiliary implantation end located at the distal end of the corresponding traction member 11, that is, the traction part 110, so as to guide the flexible neural electrode 2 to perform implantation. As shown in FIG. 5, by means of the auxiliary implantation assembly 1, after the flexible neural electrode 2 is implanted, the traction member 11 can move in the longitudinal direction along the cavity 100 of the cannula 10, so that the second physical connection mechanism can be passively separated without moving the relative position between the flexible neural electrode 2 and the target site 5 or damaging the electrode, so that the layout part 21 of the flexible neural electrode 2 can be accurately brought into the target site 5. Moreover, by providing the layout part 21 and the connection part 20 in different areas, the traction part 110 will not interfere with the electrode site 210 when the traction part 11 is physically connected with the flexible neural electrode 2.

In some embodiments, the connection part 20 of the flexible neural electrode 2 is configured to be capable of forming a flexible bending relative to the layout part 21. Forming a flexible bending structure enables the traction member 11 to be physically connected with the flexible neural electrode 2, and enables the traction member 11 to be connected at a proper angle relative to the surface of the flexible neural electrode 2. Various connection methods, such as insertion or withdrawal, are easier and less vibration is introduced to the surface.

In some embodiments, the connection part 20 of the flexible neural electrode 2 is opened with one or more connection holes 200. A single connection hole 200 is shown in FIG. 3, but this is only an example. When the flexible neural electrode implantation kit 3 is assembled, that is, when the sharp head 111 is inserted into the connection part 20, the connection hole 200 may be broken. In order to cope with the situation that a single connection hole 200 breaks during physical connection, another connection hole 200 is provided as a substitute (not shown). And in the case of broken when implantation, the substitute connection hole 200 can be used and reassembled. In the present embodiment, the connection hole 200 at the proximal end of the connection part 20 is the first choice, and the connection hole 200 at the distal end of the connection part 20 is the substitute. In addition, in order to ensure the effectiveness of the design of a plurality of connection holes 200 and/or grooves, they are arranged in sequence from the proximal end to the distal end.

In other embodiments of the present application, one or more grooves may be opened in the connection part 20 of the flexible neural electrode 2. In addition, a single connection hole 200 or groove has a diameter of 0.01-25 mm, and is located at the connection part of the flexible neural electrode 2. In addition, the distance between the adjacent connection holes or grooves is 0.01-25 mm, and the minimum distance between the connection holes or grooves and the distal edge of the flexible neural electrode 2 is 0.01-25 mm. Note that the groove may be penetrated to pass the sharp head 111, or may be scored or have a smaller thickness than the periphery, so that the sharp head 111 can easily penetrate through the same.

In some embodiments, returning to FIG. 3, the flexible neural electrode 2 comprises a proximal end part 23 connected with the layout part 21 via an interconnection lead 22. In a case where the flexible neural electrode 2 is to be implanted, the proximal end part 23 is directly supported and fixed to the outer wall of the cannula 10, or supported and fixed to the same fixing device together with the cannula 10, in a way that the layout part 21 and the interconnection lead 22 are placed outside the cannula 10, which also is detachable to the proximal end part 23. By detachably connecting the layout portion 21 and the interconnecting lead 22 with the cannula 10 in a way that they are placed outside the cannula 10, it can be realized that the relative position between the flexible neural electrode 2 and the target site 5 is not moved or the electrode is not damaged when the cannula 10 is withdrawn, and then the morphology of the implanted part of the flexible neural electrode 2 and its position relative to the target site 5 will not be affected during the operation of withdrawing the auxiliary implantation assembly 1 after the flexible neural electrode 2 is implanted.

In some embodiments of the present application, a flexible neural electrode implantation system 4 is provided. As shown in FIGS. 6 to 9, the flexible neural electrode implantation system 4 comprises a flexible neural electrode implantation kit 3 and a secondary fixing device 40 according to some embodiments of the present application. The flexible neural electrode implantation kit 3 comprises an auxiliary implantation assembly 1 and a flexible neural electrode 2 comprising a proximal end part 23 connected to the layout part 21 via an interconnection lead, and the secondary fixing device 40 comprises a base 400, and a first fixing part 401 and a second fixing part 402 each detachably locked to the base 400. The auxiliary implantation assembly 1 corresponds to the flexible neural electrode 2 one-by-one, and comprises a cannula 10 and a traction member 11. The cannula 10 has a longitudinal cavity 100, and the tube wall 101 at the distal end of the cannula 10 is configured to form a contact area larger than a first threshold in a case where the cannula 10 is fixed and contacts the distal part of the flexible neural electrode 2, so as to realize the pressing and limiting against the distal part. The traction member 11 is a member extending in the longitudinal direction, and can be such as a traction guide wire, a traction needle. The traction member 11 has appropriate rigidity and flexibility so as to guide the flexible neural electrode 2 to perform implantation according to the required position and path. The distal end of the traction member 11 is formed with a traction part 110 and is configured to form a first physical connection mechanism with the proximal end of the cannula 10, and the first physical connection mechanism can be switched between a locked state as shown in FIG. 1 and an unlocked state as shown in FIG. 2 by means of the proximal operation of the traction member 11.

Figure 8:
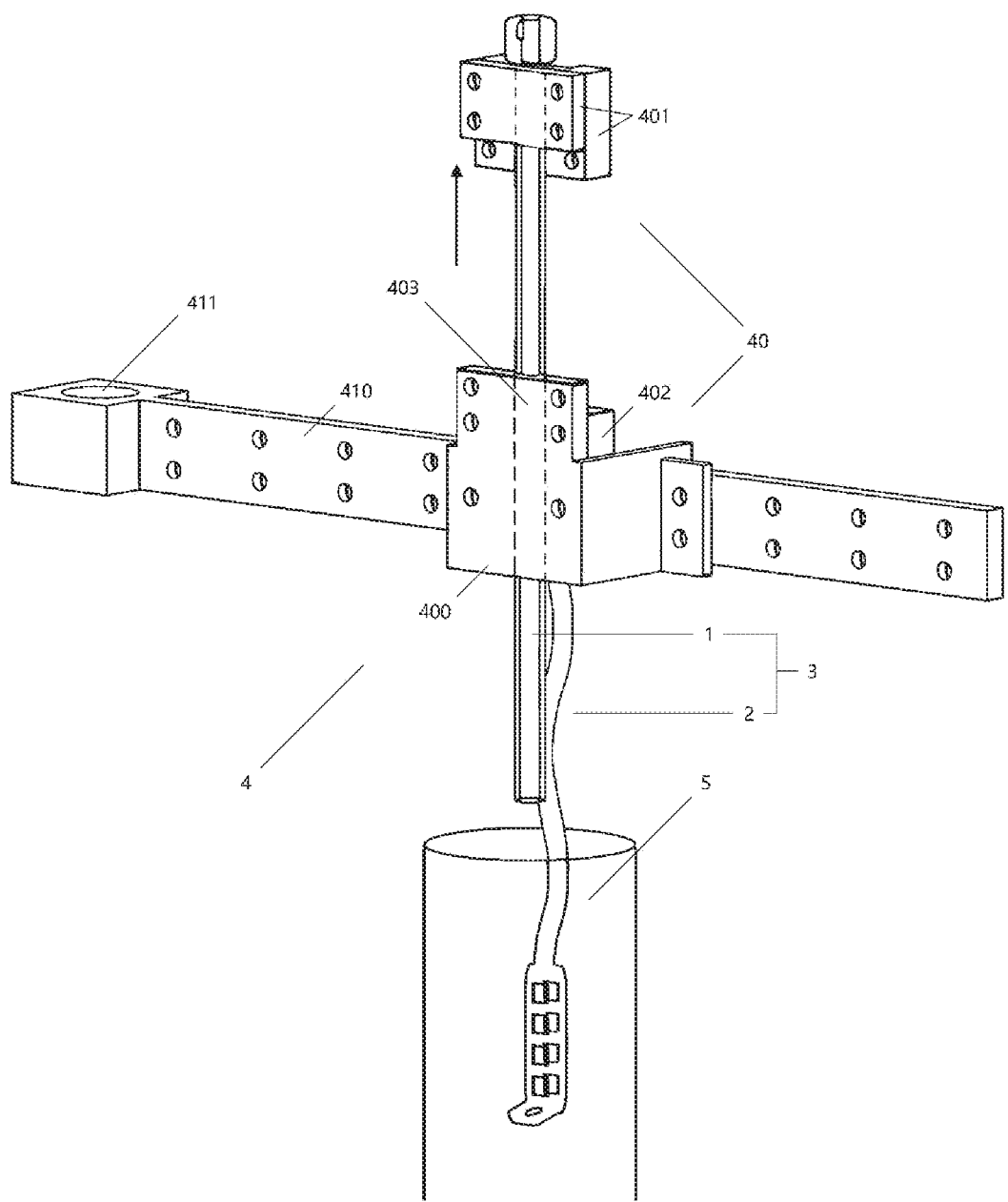
FIG. 8 is a structural schematic diagram of a first fixing part of a flexible neural electrode implantation system in an unlocked state according to an embodiment of the present application.
Figure 9:
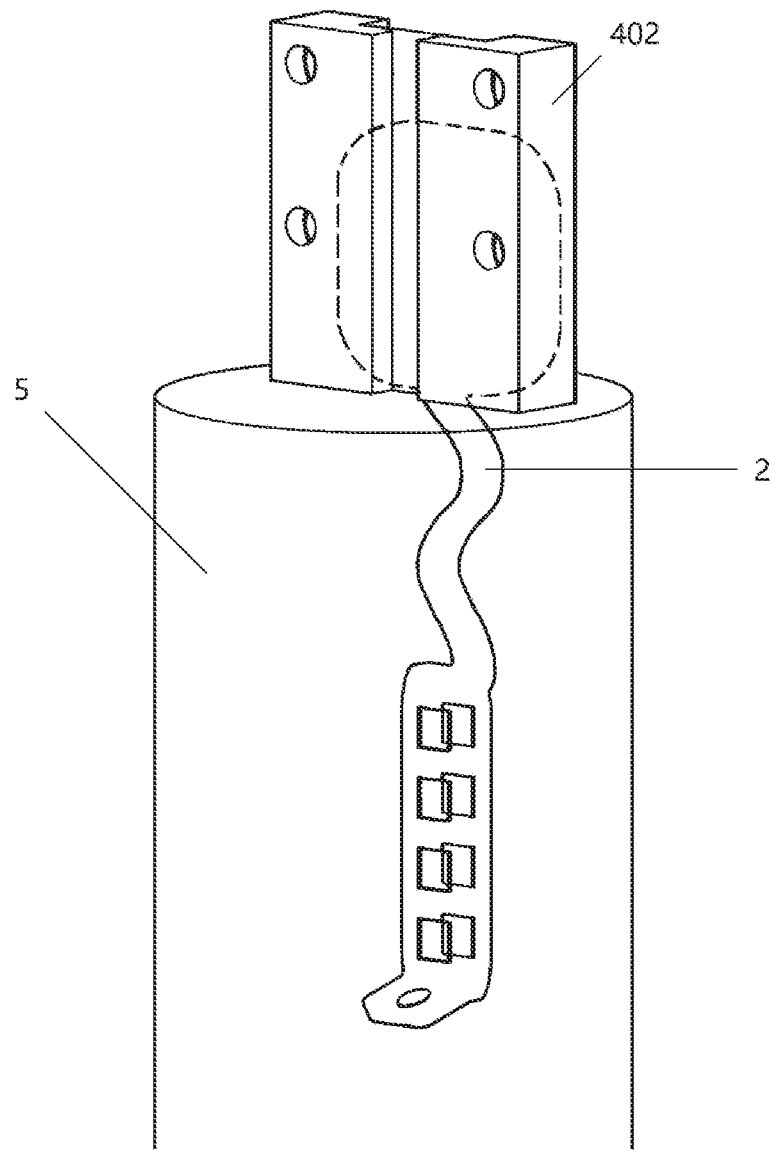
FIG. 9 is a structural schematic diagram of a second fixing part of a flexible neural electrode implantation system in an unlocked state according to an embodiment of the present application.

In some embodiments, the first fixing part 401 is configured to fix the proximal part of the cannula 10, and the second fixing part 402 is configured to fix the proximal end part 23 of the flexible neural electrode 2. As shown in FIG. 8, the first fixing part 401 is configured to be unlocked and disengaged from the base 400 to withdraw the cannula 10 from the target site 5. As shown in FIG. 9, the second fixing part 402 is configured to be unlocked and disengaged from the base 400 in a case where the cannula 10 is withdrawn and the proximal end part 23 is placed on the surface of the target site 5 or the surface of the implanted object. Only as an example, the second fixing part 402 may also be configured to be unlocked and disengaged from the base 400 in a case where the cannula 10 is withdrawn and the proximal end part 23 is placed on the surface of the target site 5 or the surface of the implanted object. By fixing the cannula 10 and the flexible neural electrode 2 in stages, the cannula 10 and the flexible neural electrode 2 can be detached in stages upon implantation, so as to improve the implantation accuracy of the flexible neural electrode 2.

In some embodiments, the base 400 or the second fixing part 402 is provided with a longitudinal chute 403, so as to facilitate the smooth withdrawal of the tube segment of the cannula 10 distal to the first fixing part 401 along the longitudinal chute 403, so that the cannula 10 can be smoothly withdrawn during disassembly without affecting the relative position of the flexible neural electrode 2 and the target site 5 or damaging the electrode.

Figure 7:
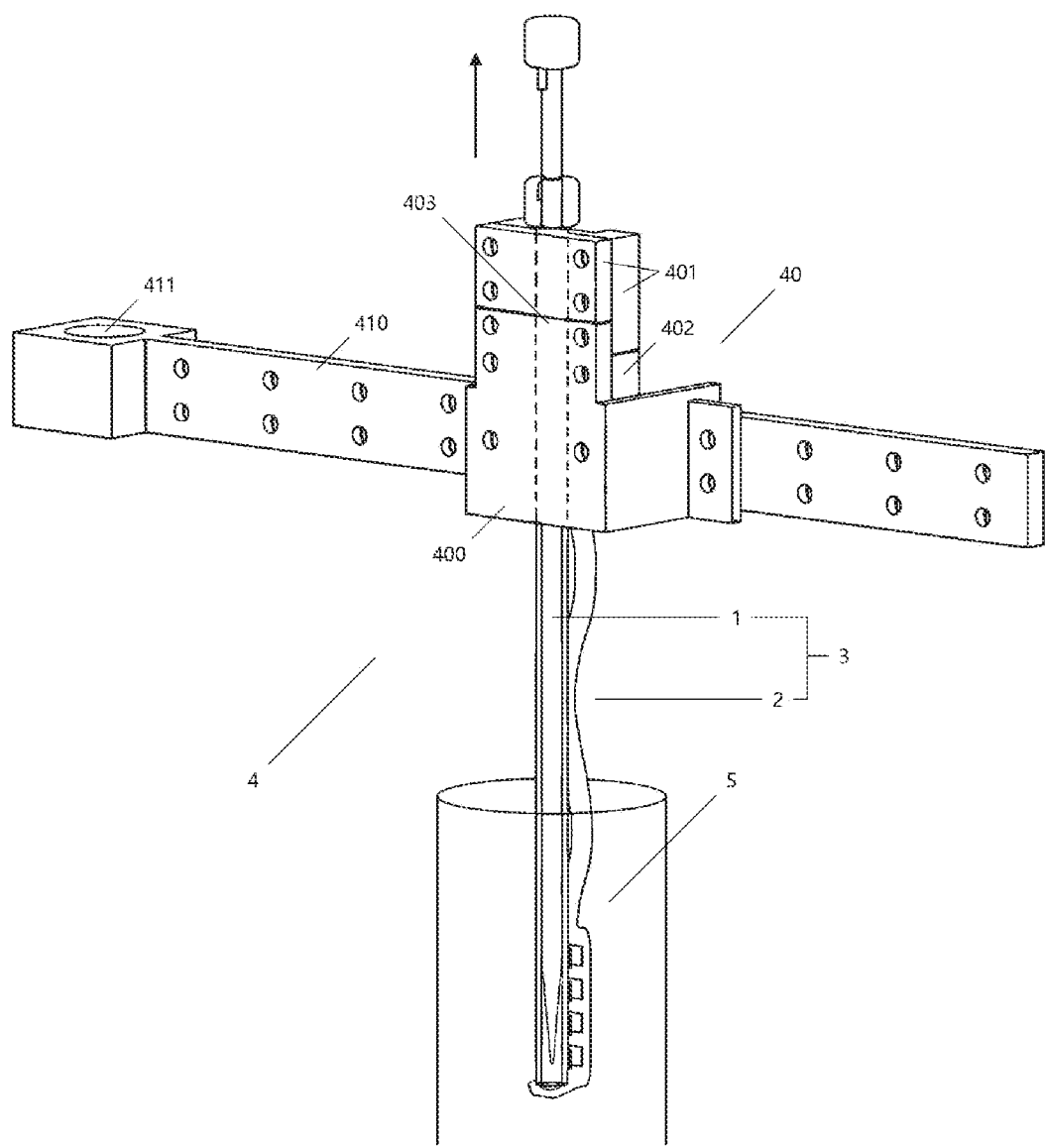
FIG. 7 is a structural schematic diagram of an auxiliary implantation assembly of a flexible neural electrode implantation system in an unlocked state according to an embodiment of the present application.

In some embodiments, the flexible neural electrode implantation system 4 further comprises a positioning implantation part (not shown), which positions the layout part 21 in real time and compares it with the medical image or medical atlas to guide the layout part 21 to reach the target site 5. The implanted part of the flexible neural electrode 2 can be brought into the target site 5 more smoothly and accurately by the positioning the implantation part. In some embodiments of the present application, the flexible neural electrode implantation kit 3 is fixed at a position of 0.01 mm-25 cm above the surface of the target site 5 by the positioning implantation part, and at the same time, the angle between the flexible neural electrode implantation kit 3 and the target site 5 is 0.01°-90°. Then, the target position where the distal part of the flexible neural electrode 2 needs to be implanted is accurately positioned by the positioning implantation part, and the flexible neural electrode implantation kit 3 is implanted at the target site 5 according to the predetermined implantation trajectory. After the distal part of the flexible neural electrode 2 reaches the predetermined position, that is, the target site 5, as shown in FIG. 7, in the unlocked state of the auxiliary implantation assembly 1, the traction member 11 is unlocked and withdrawn from the auxiliary implantation assembly 1; in the state where the first fixing part 401 is unlocked, the cannula 10 is withdrawn from the target site 5; in the state where the second fixing part 402 is unlocked, the proximal end part 23 is placed on the surface of the target site 5 or the surface of the implanted object, and the implantation process of the neural electrode is completed.

In some embodiments, the positioning implantation part further comprises a console frame (not shown) having a guide rod (not shown) movable in space and a carriage 410, and the guide rod penetrates through the connection hole 411, so that the carriage 410 is mounted on the guide rod and can move along the guide rod. In the present embodiment, the carriage 410 serves as the secondary fixing device 40, and is movable supported and fitted to the guide rod.

With the auxiliary implantation assembly, kit and system for the flexible neural electrode of the present application, when a rigid needle is used for assisting implantation, the electrode can be prevented from displacing or bringing out the implanted object when the auxiliary implantation assembly is withdrawn, thereby improving the implantation accuracy. Therefore, the present application provides a more simple, effective and accurate implantation method of the flexible neural electrode.

In the present application, the displacement of the flexible neural electrode after implantation is avoided, so that the action part of the electrode can be prevented from deviating from the target implantation area, thereby the expected measurement data or treatment effect can be obtained, and thus better treatment effect can be obtained. In addition, in the research of brain-computer interface, the flexible neural electrode is used to capture neural signals and transmit them to the computer for analysis. By avoiding the displacement of the flexible neural electrode after implantation, the signal quality can be improved, thus the accuracy of identifying and interpreting neural signals is improved.

Furthermore, although exemplary embodiments have been described herein, their scope comprises any and all embodiments with equivalent elements, modifications, omissions, combinations (e.g., solutions where various embodiments intersect), adaptations or changes based on the present application. The elements in the claims are to be broadly interpreted based on the language adopted in the claims, and are not limited to the examples described in this specification or during the implementation of the present application, and their examples are to be interpreted as non-exclusive. Therefore, the specification and examples are intended to be considered as examples only, with a true scope and spirit indicated by the following claims along with their full scope of equivalents.

The above description is intended to be illustrative rather than limiting. For example, the above examples (or one or more solutions thereof) can be used in combination with each other. For example, other embodiments may be used by those skilled in the art upon reading the above description. In addition, in the above specific embodiments, various features can be grouped together to simplify the present application. This should not be interpreted as an intention that an unclaimed disclosed feature is essential to any claim. On the contrary, the subject matter of the invention may be less than all features of a particular disclosed embodiment. Thus, the following claims are incorporated into the detailed description here as examples or embodiments, wherein each claim stands alone as a separate embodiment, and it is considered that these embodiments can be combined with each other in various combinations or permutations. The scope of the invention should be determined with reference to the appended claims along with the full scope of equivalents to which these claims are entitled.

The above embodiments are only exemplary embodiments of the present application, and are not used to limit the invention, and the protection scope of the invention is defined by the claims. Those skilled in the art can make various modifications or equivalent substitutions within the spirit and protection scope of the invention, and such modifications or equivalent substitutions should also be regarded as falling within the protection scope of the invention.

The invention claimed is:

1. An auxiliary implantation assembly for a flexible neural electrode, wherein the auxiliary implantation assembly comprises:
   a cannula having a longitudinal cavity, and a tube wall at a distal end of the cannula is configured to form a contact area larger than a first threshold to realize the pressing and limiting against the distal part in a case where the cannula is fixed and contacts a distal part of the flexible neural electrode; and
   a traction member extending in the longitudinal direction, a distal end of which is formed with a traction part and is configured to form a first physical connection mechanism with a proximal end of the cannula, the first physical connection mechanism is switchable between a locked state and an unlocked state by means of a proximal operation of the traction member relative to the cannula,
   wherein, in the locked state, the traction part penetrates out of the distal end of the cannula, and the penetrated traction part is configured to form a second physical connection mechanism with the distal part of the flexible neural electrode, so as to guide the flexible neural electrode in implantation,
   in the unlocked state, the traction member is movable in the longitudinal direction along the cavity of the cannula,
   the second physical connection mechanism is configured to separate in a case where a proximal force is applied to the traction member,
   wherein the traction member is further configured to switch the first physical connection mechanism to the unlocked state and retract proximally in the longitudinal direction along the cavity of the cannula in a case where a layout part of an electrode site of the flexible neural electrode is implanted to a target site, and
   the cannula is further configured to press and limit against the distal part via the contact between the tube wall at the distal end and the distal part, in a process of the traction member retracting proximally relative to the target site; then withdraw away from the target site in the longitudinal direction after the traction member is completely withdrawn from the target site.

2. The auxiliary implantation assembly according to claim 1, wherein an electrode site is arranged or not arranged at the distal part of the flexible neural electrode according to a layout mode of the electrode site, so that a separation of the second physical connection mechanism and the pressing and limiting of the cannula do not interfere with the electrode site.

3. The auxiliary implantation assembly according to claim 1, wherein the traction member has a sharp head to be inserted into the distal part of the flexible neural electrode, so as to form the second physical connection mechanism.

4. The auxiliary implantation assembly according to claim 3, wherein a length of the sharp head in the longitudinal direction is greater than a thickness of the distal part of the flexible neural electrode.

5. The auxiliary implantation assembly according to claim 1, wherein the second physical connection mechanism is formed by adhering the traction part and the distal part.

6. The auxiliary implantation assembly according to claim 1, wherein the traction part is formed with a grasper to grasp the distal part so as to form the second physical connection mechanism.

7. The auxiliary implantation assembly according to claim 1, wherein the cannula is further configured to, in a case where the flexible neural electrode is to be implanted, directly support and fix a proximal end part of the flexible neural electrode to an outer wall thereof, or get supported and fixed to a same fixing device together with the proximal end part, in a manner that the flexible neural electrode is placed outside the cannula, which also is detachable from the proximal end part.

8. The auxiliary implantation assembly according to claim 1, wherein a proximal end of the traction member is configured to form the first physical connection mechanism with the proximal end of the cannula, and form a T-shaped part to be snapped to the proximal end of the cannula.

9. A flexible neural electrode implantation kit comprising:
a flexible neural electrode containing the layout part of an electrode site and a connection part distal to the layout part; and
the auxiliary implantation assembly according to claim 1.

10. The flexible neural electrode implantation kit according to claim 9, wherein the connection part of the flexible neural electrode is configured to be capable of forming flexible bending relative to the layout part.

11. The flexible neural electrode implantation kit according to claim 10, wherein the flexible neural electrode comprises a proximal end part connected with the layout part via an interconnection lead, and the proximal end part is further configured to, in a case where the flexible neural electrode is to be implanted, directly support and fix to an outer wall thereof, or get supported and fixed to a same fixing device together with the cannula, in a manner that the layout portion and the interconnecting lead are placed outside the cannula, which also is detachable from the proximal end part.

12. The flexible neural electrode implantation kit according to claim 9, wherein the auxiliary implantation assemblies are multiple and distributed in an array.

13. The flexible neural electrode implantation kit according to claim 9, wherein the connection part of the flexible neural electrode is opened with a hole and/or a groove.

14. The flexible neural electrode implantation kit according to claim 13, wherein the number of the hole and/or the groove is one or more.

15. A flexible neural electrode implantation system comprising:
the flexible neural electrode implantation kit according to claim 9, the flexible neural electrode comprises a proximal end part connected with the layout part via an interconnection lead; and
a secondary fixing device comprising a base, and a first fixing part and a second fixing part which are respectively detachably locked to the base, wherein the first fixing part is configured to fix the proximal part of the cannula, and the second fixing part is configured to fix the proximal end part of the flexible neural electrode.

16. The flexible neural electrode implantation system according to claim 15, wherein the first fixing part is configured to be unlocked and disengaged from the base to withdraw the cannula from the target site.

17. The flexible neural electrode implantation system according to claim 15, wherein the second fixing part is configured to be unlocked and disengaged from the base in a case where the cannula is withdrawn and the proximal end part is to be placed on a surface of the target site or a surface of the implanted object.

18. The flexible neural electrode implantation system according to claim 15, wherein a longitudinal chute is formed on the base or the second fixing part, so as to facilitate smooth withdrawal of a tube segment of the cannula distal to the first fixing part along the longitudinal chute.

19. The flexible neural electrode implantation system according to claim 15, further comprising a positioning implantation part, wherein the positioning implantation part positions the layout part in real time and compares it with a medical image or medical atlas to guide the layout part to reach the target site.

20. The flexible neural electrode implantation system according to claim 19, wherein the positioning implantation part further comprises a console frame having a guide rod movable in space and a carriage movable along the guide rod, and the carriage is used as the secondary fixing device, and is movably supported and fitted to the guide rod.

* * * * *